(12) United States Patent
Meyrowitz

(10) Patent No.: US 7,238,373 B2
(45) Date of Patent: Jul. 3, 2007

(54) NUTRITIONAL SUPPLEMENT

(75) Inventor: Scott Meyrowitz, Dallas, TX (US)

(73) Assignee: Nutritox LLC

( * ) Notice: Subject to any disclaimer, the term of this patent is extended or adjusted under 35 U.S.C. 154(b) by 430 days.

(21) Appl. No.: 10/818,380

(22) Filed: Apr. 5, 2004

(65) Prior Publication Data

US 2004/0197430 A1    Oct. 7, 2004

Related U.S. Application Data

(60) Provisional application No. 60/460,317, filed on Apr. 4, 2003.

(51) Int. Cl.
*A61K 31/733* (2006.01)
*A61K 36/00* (2006.01)

(52) U.S. Cl. ...................... 424/655; 602/614

(58) Field of Classification Search .................. None
See application file for complete search history.

(56) References Cited

OTHER PUBLICATIONS

Phillipson, J. New Drugs From Nature—It Could be Yew; Phytotherapy Research 13 (1999) pp. 2-8.*

Revilla et al. Comparison of Several Procedures Used for the Extraction of Anthocynains From Red Grapes; J. Agric. Food Chem. 1998, 46, pp. 4592-4597.*

Marketing Intelligence Service Ltd. Renew Life Cleansesmart All Natural System; Product Alert, May 10, 1999, vol. 29, No. 9, one page.*

Smartbomb.com; Renew Life Daily Multi-Cleanse 30 Day; URL <www.smartbomb.com/rl53524.html> accessed Jul. 27, 2006.*

Weed, S. Weed Wanderings: Menopausal Years: URL <http://www.susanweed.com/herbal_ezine/September04/menopausal.htm> accessed Jan. 18, 2007, pp. 1-9.*

Parsley- Petroselinum Crispum, History & Mythology: URL <http://www.selfsufficientish.com/parsley.htm> accessed Jan. 18, 2007, pp. 1-4.*

PR Newswire: Calci-Yum 100% BONE-afide YUM . . . Sep. 6, 2001, p. 1 (pp. 1-2 of ProQuest).*

* cited by examiner

*Primary Examiner*—Patricia Leith

(57) ABSTRACT

A nutritional supplement is provided that is designed to provide nutritional benefits as well as to assist the body with detoxification. By providing a supplement that serves both of these functions, the present invention may enable persons to improve their overall wellness.

5 Claims, 1 Drawing Sheet

NUTRITIONAL SUPPLEMENT

REFERENCE TO PRIOR APPLICATION

Figure 1:
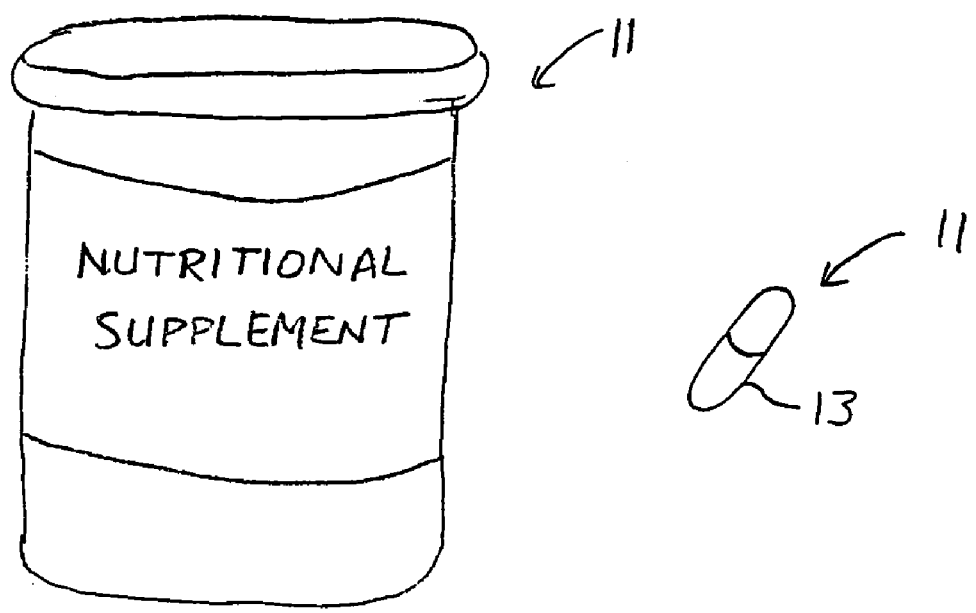

This application claims the benefit of U.S. Provisional Application No. 60/460,317, filed Apr. 4, 2003.

BACKGROUND OF THE INVENTION

1. Field of the Invention

This invention relates generally to a nutritional supplement and in particular to a nutritional supplement having nutritional, as well as detoxification, components.

2. Description of Related Art

With the American Medical Association's recent recommendation of multivitamins for all adults for health and prevention of chronic disease, many people have turned to vitamins for improving their health. Studies show taking a multivitamin daily can help boost energy levels, improve immunity, and promote overall health. The critical factors in selecting high quality multivitamins and supplements are high nutrient levels, absorbability, and guaranteed quality assurance.

Many people mistakenly assume a one-a-day multivitamin provides everything they need. However, it is virtually impossible to fit adequate levels of vitamins and minerals into one pill, and therefore most one-a-day multivitamins only contain the Recommended Daily Allowance (RDA) of nutrients. While RDAs reflect nutrient levels necessary to prevent deficiencies, they do not necessarily indicate amounts required to promote health.

Optimum nutrient levels are not the only important factor in selecting a multivitamin. A supplement must also provide vitamins and minerals in an absorbable form. For example, many currently-available supplements contain synthetic Vitamin E, which the body does not absorb as readily as the natural form of the vitamin.

One characteristic that is missing from currently-available nutritional supplements is a detoxifying component. With constant exposure to toxins in food, water, and the air, enormous stress is placed on the body. Detoxification is often an overlooked component that is essential to total wellness.

A need therefore exists for a nutritional supplement that provides high levels of nutrients in absorbable form and that maintains high levels of quality and purity. A need further exists for a nutritional supplement that provides a detoxification component for helping eliminate toxins ingested by the body.

DETAILED DESCRIPTION OF THE PREFERRED EMBODIMENT

In the following detailed description of the preferred embodiments, reference is made to the accompanying drawings which form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical mechanical and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

A nutritional supplement 11 according to the present invention is preferably encapsulated by a water-soluble capsule. Capsules are used to deliver the nutritional supplement because capsules are generally better absorbed than tablets. Although properly manufactured tablets should dissolve in the presence of stomach acids and could be used to deliver the nutritional supplement of the present invention, people with low-acidity or poor digestion may not be able to break down the tablet in their system. Another reason for using capsules is that tablets are pressed using pressure and high heat, which may destroy active ingredients and compromise potency of the supplement.

The nutritional supplement 11 is described herein for three examples: an Adult Male Formula, an Adult Female Formula, and an Athletic Formula.

The Adult Male Formula provides optimal amounts of absorbable vitamins and minerals to meet the unique nutritional requirements of men. Also included are Korean ginseng for energy and saw palmetto and lycopene for a healthy prostate. A listing of the preferred supplemental ingredients and amounts of the Adult Male Formula example are listed in Table 1. Amounts are given based on a serving size of four capsules. As will be appreciated by those of ordinary skill in the art, "IU" refers to "international units", "mg" refers to "milligrams", and "mcg" refers to "micrograms".

TABLE 1

| Ingredient | Amount Per Serving |
| --- | --- |
| Vitamin A (5000 IU as beta carotene, 2500 IU as retinyl palmitate) | 7500 IU |
| Vitamin C (as ascorbic acid and ascorbyl palmitate) | 300 mg |
| Vitamin D (as cholecalciferol) | 400 IU |
| Vitamin E (as d-alpha tocopheryl succinate and mixed tocopherols) | 100 IU |
| Vitamin K | 30 mcg |
| Thiamin (as thiamin HCl) | 35 mg |
| Riboflavin | 20 mg |
| Niacin (as niacinamide and niacin) | 65 mg |
| Vitamin B-6 (as pyridoxine HCL) | 20 mg |
| Folic Acid | 800 mcg |
| Vitamin B-12 (as cyanocobalamin) | 300 mcg |
| Biotin | 300 mcg |
| Pantothenic Acid (as calcium pantothenate) | 45 mg |
| Calcium (as calcium carbonate and calcium citrate/malate) | 300 mg |
| Iodine (from Atlantic kelp) | 150 mcg |
| Magnesium (as magnesium oxide and magnesium citrate) | 250 mg |
| Zinc (as zinc amino acid chelate) | 25 mg |
| Selenium (as L-selenomethionine) | 200 mcg |
| Copper (as copper amino acid chelate) | 2 mg |
| Manganese (as manganese gluconate) | 2 mg |
| Chromium (as chromium polynicotinate) | 200 mcg |
| Molybdenum (as sodium molybdate) | 25 mcg |
| Potassium (as potassium citrate) | 99 mg |
| Boron (as boron citrate) | 1 mg |
| Choline (as choline bitartrate) | 25 mg |
| Saw Palmetto berry extract (25% fatty acids) | 50 mg |
| Panax Ginseng root extract (standardized to 8% ginsenosides) | 25 mg |
| Lycopene | 2 mg |

The Adult Male Formula example also includes a detoxification blend which assists in removing toxins from the body. The preferred ingredients and amounts for these components are listed in Table 2. Again, the amounts listed are based on a serving size of four capsules.

TABLE 2

DAILY DETOX BLEND

| Ingredient | Amount Per Serving |
| --- | --- |
| Milk Thistle seed extract (standardized to 80% silymarin) | 40 mg |
| Alpha Lipoic Acid | 40 mg |
| Calcium d-Glucarate | 25 mg |
| Turmeric root extract (standardized to 95% curcuminoids) | 50 mg |
| N-Acetyl Cysteine | 100 mg |
| Inulin | 200 mg |

The Adult Female Formula example according to the present invention offers a complete range of well-absorbed vitamins and minerals to meet the special nutritional needs of women of all ages. Higher amounts of calcium and magnesium help promote strong healthy bones. Also included are green tea extract for antioxidant power, chaste tree berry and black cohosh for hormonal balance, and cranberry for urinary tract health. A listing of the preferred supplemental ingredients and amounts of the Adult Female Formula example are listed in Table 3. Amounts are given based on a serving size of four capsules.

TABLE 3

| Ingredient | Amount Per Serving |
| --- | --- |
| Vitamin A (5000 IU as beta carotene, 2500 IU as retinyl palmitate) | 7500 IU |
| Vitamin C (as ascorbic acid and ascorbyl palmitate) | 300 mg |
| Vitamin D (as cholecalciferol) | 400 IU |
| Vitamin E (as d-alpha tocopheryl succinate and mixed tocopherols) | 100 IU |
| Vitamin K | 30 mcg |
| Thiamin (as thiamin HCl) | 35 mg |
| Riboflavin | 20 mg |
| Niacin (as niacinamide and niacin) | 65 mg |
| Vitamin B-6 (as pyridoxine HCl) | 40 mg |
| Folic Acid | 800 mcg |
| Vitamin B-12 (as cyanocobalamin) | 300 mcg |
| Biotin | 300 mcg |
| Pantothenic Acid (as calcium pantothenate) | 45 mg |
| Calcium (as calcium carbonate and calcium citrate/malate) | 500 mg |
| Iodine (from Atlantic kelp) | 150 mcg |
| Magnesium (as magnesium oxide and magnesium citrate) | 250 mg |
| Zinc (as zinc amino acid chelate) | 15 mg |
| Selenium (as L-selenomethionine) | 200 mcg |
| Copper (as copper amino acid chelate) | 1 mg |
| Manganese (as manganese gluconate) | 2 mg |
| Chromium (as chromium polynicotinate) | 200 mcg |
| Molybdenum (as sodium molybdate) | 25 mcg |
| Potassium (as potassium citrate) | 99 mg |
| Boron (as boron citrate) | 2 mg |
| Choline (as choline bitartrate) | 25 mg |
| Chaste Tree berry extract (4:1) | 25 mg |
| Green Tea leaf extract (50% polyphenols) | 25 mg |
| Black Cohosh root extract (standardized to 2.5% triterpene glycosides) | 5 mg |
| Cranberry powder | 25 mg |

The Adult Female Formula example also includes a detoxification blend which assists in removing toxins from the body. The preferred ingredients and amounts for these components are listed in Table 4. Again, the amounts listed are based on a serving size of four capsules.

TABLE 4

DAILY DETOX BLEND

| Ingredient | Amount Per Serving |
| --- | --- |
| Milk Thistle seed extract (standardized to 80% silymarin) | 40 mg |
| Alpha-Lipoic Acid | 40 mg |
| Calcium d-Glucarate | 25 mg |
| Turmeric root extract (standardized to 95% curcuminoids) | 50 mg |
| N-Acetyl Cysteine | 100 mg |
| Inulin | 200 mg |

The Athletic Formula example according to the present invention is directed to both active men and women and provides a complete range of essential vitamins and minerals to meet an athlete's unique nutritional needs. This formula contains MSM for joint health, malic acid for cellular energy production, and higher levels of antioxidant nutrients. Intense exercise increases the production of cell-damaging free radicals, which antioxidants help neutralize. A listing of the preferred supplemental ingredients and amounts of the Athletic Formula is provided in Table 5. Amounts are given based on a serving size of six capsules.

TABLE 5

| Ingredient | Amount Per Serving |
| --- | --- |
| Vitamin A (as 50% beta carotene, 50% retinyl palmitate) | 10,000 IU |
| Vitamin C (as ascorbic acid) | 1000 mg |
| Vitamin D (as cholecalciferol) (D3) | 400 IU |
| Vitamin E (as d-alpha tocopheryl succinate and mixed tocopherols) | 300 IU |
| Vitamin K | 30 mcg |
| Vitamin B1 (as thiamine HCl) | 35 mg |
| Vitamin B2 (as riboflavin) | 20 mg |
| Vitamin B3 (as 40% niacin, 60% niacinamide) | 75 mg |
| Vitamin B6 (as pyridoxine HCl) | 20 mg |
| Pyridoxal-5-Phosphate | 5 mg |
| Folic Acid | 800 mcg |
| Vitamin B-12 (as cyanocobalamin) | 500 mcg |
| Biotin | 300 mcg |
| Pantothenic Acid (as calcium pantothenate) | 100 mg |
| Calcium (as calcium amino acid chelate) | 300 mg |
| Iodine (as kelp) | 150 mcg |
| Magnesium (as magnesium aspartate) | 250 mg |
| Zinc (as zinc amino acid chelate) | 25 mg |
| Selenium (as seleno-L-methionine) | 200 mcg |
| Copper (as copper amino acid chelate) | 2 mg |
| Manganese (as manganese amino acid chelate) | 5 mg |
| Chromium (as chromium polynicotinate) | 200 mcg |
| Potassium (as potassium amino acid chelate) | 99 mg |
| Boron (as boron aspartate) | 1 mg |
| Choline (as choline bitartrate) | 25 mg |
| Malic Acid | 300 mg |
| MSM (methylsulfonylmethane) | 250 mg |
| TMG (trimethylglycine) | 100 mg |

The Athletic Formula example also includes a detoxification blend which assists in removing toxins from the body. The preferred ingredients and amounts for these components are listed in Table 6. Again, the amounts listed are based on a serving size of six capsules.

TABLE 6

DAILY DETOX BLEND

| Ingredient | Amount Per Serving |
| --- | --- |
| Silymarin (from standardized milk thistle extract) (*silibum marianum*) (seed) | 40 mg |
| Alpha-Lipoic Acid | 40 mg |
| Calcium d-Glucarate | 25 mg |
| Tumeric Extract (95% curcuminoids) (*curcuma longa*) (root) | 50 mg |
| N-Acetyl Cysteine | 100 mg |
| Inulin | 200 mg |

Descriptions of the ingredients contained in the Adult Male Formula, the Adult Female Formula, and the Athletic Formula examples are provided in the following paragraphs.

Vitamin A (as 50% beta-carotene, 50% retinyl palmitate). Half of the vitamin A in this multiple is in the form of beta-carotene, an important antioxidant and immune system booster. Beta-carotene is water-soluble and converts to vitamin A as needed in the body. There are 5,000 I.U. of actual vitamin A in the form of retinyl palmitate. Vitamin A plays an essential role in vision, skin health, and immunity. A good multiple supplies both beta-carotene and preformed vitamin A.

Vitamin C (as ascorbic acid and ascorbyl palmitate) functions as a powerful antioxidant and immune system supporter. This formula contains both the water and fat-soluble forms of C, enabling it to work in more cells in the body. Vitamin C plays a major role in the synthesis of collagen, the main structural protein of joints, skin, bone, gums and blood vessels. It also helps the body handle all different types of stress because it assists in making various stress hormones. Although only a few milligrams daily are necessary to prevent a deficiency disease (i.e. scurvy), much higher levels in divided doses help reap the full benefits of vitamin C's antioxidant properties.

Vitamin D3 (as cholecalciferol) in this form is considerably more active than vitamin D2 (ergocalciferol). This fat-soluble nutrient is necessary for calcium absorption in the intestines. Vitamin D intake has been inversely associated with certain forms of cancer, including breast, prostate, and colorectal cancer.

Vitamin E (as d-alpha tocopheryl succinate and mixed tocopheryls) is a powerful antioxidant that is vital in maintaining heart health, as evidenced by the Cambridge Heart Antioxidant Study. Supplementation of vitamin E is important because dietary sources (e.g. almonds, pecans, and wheat germ oil) contain only small amounts. Vitamin E is actually a family of different compounds. Although d-alpha tocopherol is the most active antioxidant, increasing research indicates that other tocopherols, especially gamma-tocopherol, are also beneficial. This multiple has vitamin E as mixed tocopherols, the way nature intended, instead of only alpha-tocopherol. The vitamin E used in the nutritional supplement (d-alpha tocopherol) is absorbed much better than the synthetic form (dl-alpha tocopherol).

The importance of Vitamin K is often overlooked, but it is critical for strong healthy bones. Vitamin K is also necessary for proper blood clotting. The best dietary sources include green leafy vegetables, such as spinach, kale, collards, and broccoli. The greener the plant, the higher the K content. Additionally, "friendly" bacteria found in the intestines manufacture K.

Vitamin B-1 (as thiamin HCL) plays a major role in converting carbohydrates from food into energy. It is also involved in maintaining muscular function, especially the heart. B-1 deficiency impairs the brain's ability to produce acetylcholine, a primary brain chemical involved in memory. Alcohol interferes with its absorption. Because vitamin B-1 is water-soluble, it is not stored in the body and needs to be replenished daily.

Vitamin B-2 (riboflavin) plays a critical role in converting food into energy and is involved in several enzymatic pathways. It is naturally fluorescent yellow and can easily turn the urine a bright yellow color if even a small amount is excreted from the body. Intense exercise and oral contraceptives increase the need for riboflavin, along with all other B vitamins.

Vitamin B-3 (as niacinamide and niacin) is the common name for two compounds: niacin and niacinamide. Both have similar functions and are involved in over 200 different reactions in the metabolism of carbohydrates, fat, and protein. However, only niacin (not niacinamide) is effective in promoting healthy cholesterol levels. This multiple contains both beneficial forms because high levels of niacin may cause an unpleasant flushing effect.

Vitamin B-6 (as pyridoxine HCL) is necessary for protein synthesis (i.e. muscle growth). Increased protein consumption raises B-6 requirements. It is also necessary for the production of serotonin, often called the "feel-good" hormone. Vitamin B-6, along with folic acid and vitamin B-12, are "heart healthy" because of their role in reducing homocysteine, an amino acid that promotes heart disease.

Pyridoxal-5-Phosphate (P-5-P) is the active form of vitamin B-6.

Folic Acid is a B vitamin important for heart health due to its role in regulating homocysteine levels. Elevated homocysteine is linked to heart disease and Alzheimer's disease. Deficiency during early pregnancy significantly increases the risk for neural tube defects. Although folic acid is nontoxic, mega doses can mask an underlying vitamin B-12 deficiency. Interestingly, supplemental folic acid is better absorbed than food sources.

Vitamin B-12 (cyanocobalamin) is important for cellular energy production and plays a major role in the functioning of the nervous system. Vegetarians are at a higher risk for deficiency because it is only available in animal sources. The elderly also have an increased risk for B-12 deficiency due to compromised absorption.

Biotin is a B vitamin best known for its role in promoting hair and nail growth and strength. "Friendly" bacteria in the small intestines are able to produce small amounts biotin. Many enzymes involved in carbohydrate and fat metabolism contain this vitamin.

Pantothenic Acid (as calcium pantothenate) is a B vitamin that participates in a wide variety of reactions in the body. It is involved in releasing energy from dietary carbohydrates, synthesizing various hormones and metabolizing alcohol. Because it is widely available in food, deficiency is rare.

Calcium (as calcium carbonate and calcium citrate/malate) is best known for its role in the development and maintenance of healthy bones and teeth, where 99% of it is stored. However, the remaining 1% of calcium in the blood is critical for proper muscle contraction, blood pressure regulation, and nerve function. Dietary intake is frequently sub-optimal.

Iodine (from Atlantic kelp) is required for thyroid hormone synthesis. It is a trace mineral, meaning only small amounts are needed by the body.

Magnesium (as magnesium oxide and magnesium citrate) is one of the most important minerals and helps activate over 300 enzyme systems in the body. Unfortunately, many multiples on the market contain only insignificant amounts of magnesium. Magnesium is vital for energy production and carbohydrate metabolism. It also influences calcium metabolism and is involved in bone health and muscle function. Good dietary sources include dark leafy green vegetables, tofu, and legumes. Sub-optimal magnesium intake is frequently cited in national food surveys. Food processing removes the majority of the magnesium found in grains.

Zinc (as zinc amino acid chelate) is an excellent immune system booster. Zinc is also needed for muscle growth, insulin function, vision, and taste perception. It supports prostate health and the body's ability to protect itself against heavy metal toxicity, such as cadmium and lead. Large doses of zinc can deplete copper.

Selenium (as L-selenomethionine) is a powerful antioxidant and significantly increases the effectiveness of vitamin E. It also contains antiviral properties and plays an important role in prostate, lung, and breast health. The amount of selenium found in plant foods directly depends on the concentration of selenium in the soil. Areas containing lower levels of soil selenium have been linked to higher incidences of certain cancers and heart disease. Selenium helps protect against heavy metal toxicity, especially mercury. A quality multiple vitamin & mineral formula should contain approximately 100-200 mcg of selenium per day. The seleno-L-methionine form of selenium is highly bioavailable and preferred over the cheaper sodium selenite.

Copper (as copper amino acid chelate) plays a role in transporting oxygen throughout the body. The production of collagen, which determines the integrity of bones, skin, cartilage, and tendons, is copper dependent. Copper is also crucial for making melanin, which provides color to skin and hair.

Manganese (as manganese gluconate) is needed for bone, joint, and skin integrity. It is a component of several enzymes, including the powerful antioxidant SOD (superoxide dismutase).

Chromium (as chromium polynicotinate) is a supercritical mineral that is vital for blood sugar balance and carbohydrate metabolism. The chromium polynicotinate form is a niacin-bound chromium that is exceptionally well absorbed. Niacin has synergistic effects with chromium. This form is superior to the more popular chromium picolinate. A quality multiple for adults should contain approximately 200 mcg of chromium polynicotinate.

Molybdenum (sodium molybdate) is an essential trace mineral that is required for several enzymatic reactions in the body. Deficiency is rare.

Potassium (as potassium citrate) is one of the body's primary electrolytes. Many Americans do not consume optimal amounts of potassium because of their inadequate intake of wholesome fruits and vegetables. Deficiency can cause muscle weakness, cramps, fatigue, mental confusion, heart disturbances, and bloating.

Boron (as boron citrate) is an overlooked mineral essential for bone health. It reduces urinary loss of calcium. Plant foods generally contain more boron than animal sources.

Choline (as choline bitartrate) is used by the body to make the neurotransmitter acetylcholine for memory and concentration. Choline also provides structure to cell walls and assists in breaking up fat in the liver during fat metabolism.

Saw Palmetto berry extract (standardized to 25% fatty acids) are natural substances found in the berries of the saw palmetto plant that promote prostate health and may support healthy urinary flow.

Panax Ginseng root extract (standardized to 8% ginsenosides), also known as Asian ginseng, has been an important component of traditional Chinese medicine for over 2,000 years. The ginsenosides (concentrated in the root) have been found in studies to increase overall mental and physical vitality. Some studies also suggest Panax ginseng may enhance sexual function.

Lycopene is a member of the carotenoid family, which includes beta-carotene, and is best known for its ability to help maintain healthy prostate cells. Lycopene has antioxidant capabilities, and early research show positive effects on heart health and immunity.

Chastetree berry extract (4:1), commonly referred to as vitex, helps support female hormonal balance. Studies suggest this herb has a progesterone-like effect, which may account for its use in the support of women's health. Because of this activity, the herb is used for a variety of female complaints, including premenstrual syndrome (PMS).

Green Tea leaf extract (standardized to 50% polyphenols) has a variety of health benefits. It is best known for its potent antioxidant capabilities, which are mostly attributed to the polyphenols found in the extract. Studies also indicate the beneficial compounds found in green tea promote heart health, immunity, and healthy cells in breast tissue. Early research suggest it may play a role in enhancing thermogenesis (fat loss).

Black Cohosh root extract (standardized to 2.5% triterpene glycosides) is a plant with a history of use in North American Indian medicine for a variety of purposes. Today, it is known for its role in supporting female hormonal balance.

Cranberry powder possesses antioxidant benefits, and it may also promote urinary tract health. Studies have shown that cranberry can keep *E. coli* (the most common bacterial cause of bladder infections) from adhering to the lining of the bladder.

Malic Acid plays a critical role in producing energy in the cell. The combination of malic acid and magnesium helps combat fatigue.

MSM (Methylsulfonylmethane) is a biological form of sulfur that promotes healthy joints. Although its importance is often overlooked, sulfur is vital for the repair and maintenance of joints and other connective tissues such as hair, skin, and bones. Early research conducted at UCLA showed that supplementation with MSM helped improved joint pain in 80% of the arthritic study participants.

TMG (Trimethyglycine) is derived from beets and is an active methyl donor, making it beneficial for promoting energy production, DNA synthesis, and healthy homocysteine levels. Homocysteine is a sensitive marker for heart disease and has been recently associated with Alzheimer's disease.

Milk Thistle Extract (standardized to 80% silymarin) is the most commonly recommended herb to improve the liver's ability to detoxify harmful toxins and overall function. The liver is the body's most important detoxifying organ. Silymarin, the active ingredient in milk thistle, consists of four different compounds. Research indicates silymarin can even help reverse severe liver damage.

Alpha-Lipoic Acid (ALA) has several benefits. Known as the "ultimate antioxidant," ALA has the ability to recycle the body's use of other antioxidants, including vitamin C, vitamin E, and the powerful glutathione. Because it is uniquely both water and fat soluble, it can work in more areas of the body. ALA assists the body in eliminating everyday toxins, such as mercury. Additionally, cellular energy production, carbohydrate metabolism, and blood sugar balance are dependent on alpha-lipoic acid.

Calcium-d-glucarate is a natural substance that assists in eliminating certain toxic chemicals and excess hormones, such as environmental estrogen from plastics. This ingredient inhibits an enzyme called beta-glucuronidase (found in certain bacteria in the gut). One of the main ways the body eliminates toxins and hormones is by binding them to glucuronic acid in the liver and then excreting the complex in the bile. Beta-glucuronidase breaks the bond between the toxin and glucuronic acid, allowing the body to reabsorb the toxin. Calcium-d-glucarate helps keep beta-glucuronidase from doing this. Higher beta-glucuronidase activity is associated with an increased risk of hormone-dependent cancers, such as prostate, breast, and colon cancers.

Turmeric Extract (Curcuma longa) (containing 95% curcuminoids), also known as curcumin, is a spice with various advantageous qualities. In addition to being an effective anti-inflammatory herb, turmeric has potent antioxidant and liver protective effects to help counteract daily toxins. Interesting recent studies suggest turmeric may be helpful in minimizing damage from radiation and certain prescription medications.

N-Acetyl Cysteine (NAC) is a special form of the amino acid cysteine. NAC promotes healthy lungs and assists the body's daily battle against car exhaust, cigarette smoke and other environmental pollutants. NAC works by supercharging glutathione, a powerful detoxifier and antioxidant. Glutathione levels decrease with age.

Inulin is found in small amounts in various plant foods, such as the chicory root. Inulin is a type of fiber that helps boost the immune system. It does this by feeding the growth of probiotics ("friendly bacteria") in the colon that help crowd out bad bacteria, such as E. coli and Salmonella. The colon's "friendly bacteria" is necessary for proper digestion by improving gut integrity.

In a preferred embodiment of the invention, the daily serving sizes for the Male and Female Formulas are four capsules, and the capsules are to be taken twice daily with meals. The Athletic Formula has a daily serving size of six capsules, to be taken twice daily with food.

A person having ordinary skill in the art will recognize that the nutrient levels provided by the nutritional supplement often far exceed the Recommended Dietary Allowance (RDA). The RDAs are the average daily level of nutrients required to prevent a nutrient deficiency disease in nearly all healthy people (e.g. scurvy caused by a vitamin C deficiency). While the RDAs may establish the level of nutrients required to prevent a deficiency, they do not define the level of nutrients needed to promote optimum health. Many health experts are changing their view of vitamins and minerals as nutrients that simply prevent deficiency diseases and are instead recognizing the nutrient's role in promoting optimum health. The recommended levels of many nutrients for a person's best health will often exceed the RDAs.

In addition to the unique combination of ingredients described above, the nutritional supplement of the present invention provides exceptional quality and purity not seen in some other supplements. The nutritional supplement is manufactured, packaged, stored, and distributed in compliance with Good Manufacturing Practices (GMPs) established by the Food and Drug Administration (FDA), which assures high standards for product quality and consistency.

A person having ordinary skill in the art will recognize that the detoxification components of the nutritional supplement provide an exceptional advantage. The detoxification ingredients are included to assist the body in processing and combating toxins that are encountered in food, water, and air. Another advantage is provided by the delivery of the nutritional supplement in a capsule form to maximize absorption in the body. Finally, the manufacturing and packaging of the nutritional supplement provides further advantages by promoting quality, purity, and consistency in the product.

It should be apparent from the foregoing that an invention having significant advantages has been provided. While the invention is shown in only a few of its forms, it is not just limited but is susceptible to various changes and modifications without departing from the spirit thereof.

I claim:

1. A nutritional supplement providing for detoxification, said nutritional supplement comprising:
   Vitamin C;
   Alpha Lipoic Acid;
   Calcium d-Glucarate;
   n-Acetyl Cysteine;
   Inulin;
   Vitamin A;
   Vitamin D;
   Vitamin E;
   Vitamin K;
   Thiamin;
   Riboflavin;
   Niacin;
   Vitamin B-6;
   Folic Acid;
   Vitamin B-12;
   Biotin;
   Pantothenic Acid;
   Calcium;
   Iodine;
   Magnesium;
   Zinc;
   Selenium;
   Copper;
   Manganese;
   Chromium;
   Potassium;
   Boron; and
   Choline.

2. The nutritional supplement of claim 1 further comprising Molybdenum; and Lycopene.

3. The nutritional supplement of claim 1 further comprising:
   Molybdenum; and
   Cranberry powder.

4. The nutritional supplement of claim 1 further comprising:
   Pyridoxal-5-Phosphate;
   Malic Acid;
   Methylsulfonylmethane; and
   Trimethyglycine.

5. The nutritional supplement of claim 1 wherein the nutritional supplement is in the form of a capsule for oral ingestion.

* * * * *